United States Patent [19]
Aneja

[11] 4,374,283
[45] Feb. 15, 1983

[54] PURIFICATION OF AQUEOUS EFFLUENT STREAMS CONTAINING BPA AND PHENOL

[75] Inventor: Viney P. Aneja, Schenectady, N.Y.

[73] Assignee: General Electric Company, Schenectady, N.Y.

[21] Appl. No.: 277,421

[22] Filed: Jun. 25, 1981

[51] Int. Cl.³ .............................................. C07C 37/72
[52] U.S. Cl. .................................. 568/724; 568/749; 568/751
[58] Field of Search ................ 568/724, 749, 750, 751

[56] References Cited

U.S. PATENT DOCUMENTS

3,894,095  7/1975  Pietzsch et al. ..................... 568/748

FOREIGN PATENT DOCUMENTS

165  1/1979  European Pat. Off. ............ 568/724
49-48545  12/1974  Japan ................................... 568/724

*Primary Examiner*—Werren B. Lone
*Attorney, Agent, or Firm*—Richard J. Traverso; James C. Davis, Jr.; James Magee, Jr.

[57] ABSTRACT

A method for a purifying aqueous effluent streams containing BPA and phenol using liquid-liquid extraction with methyl isobutyl ketone.

8 Claims, 1 Drawing Figure

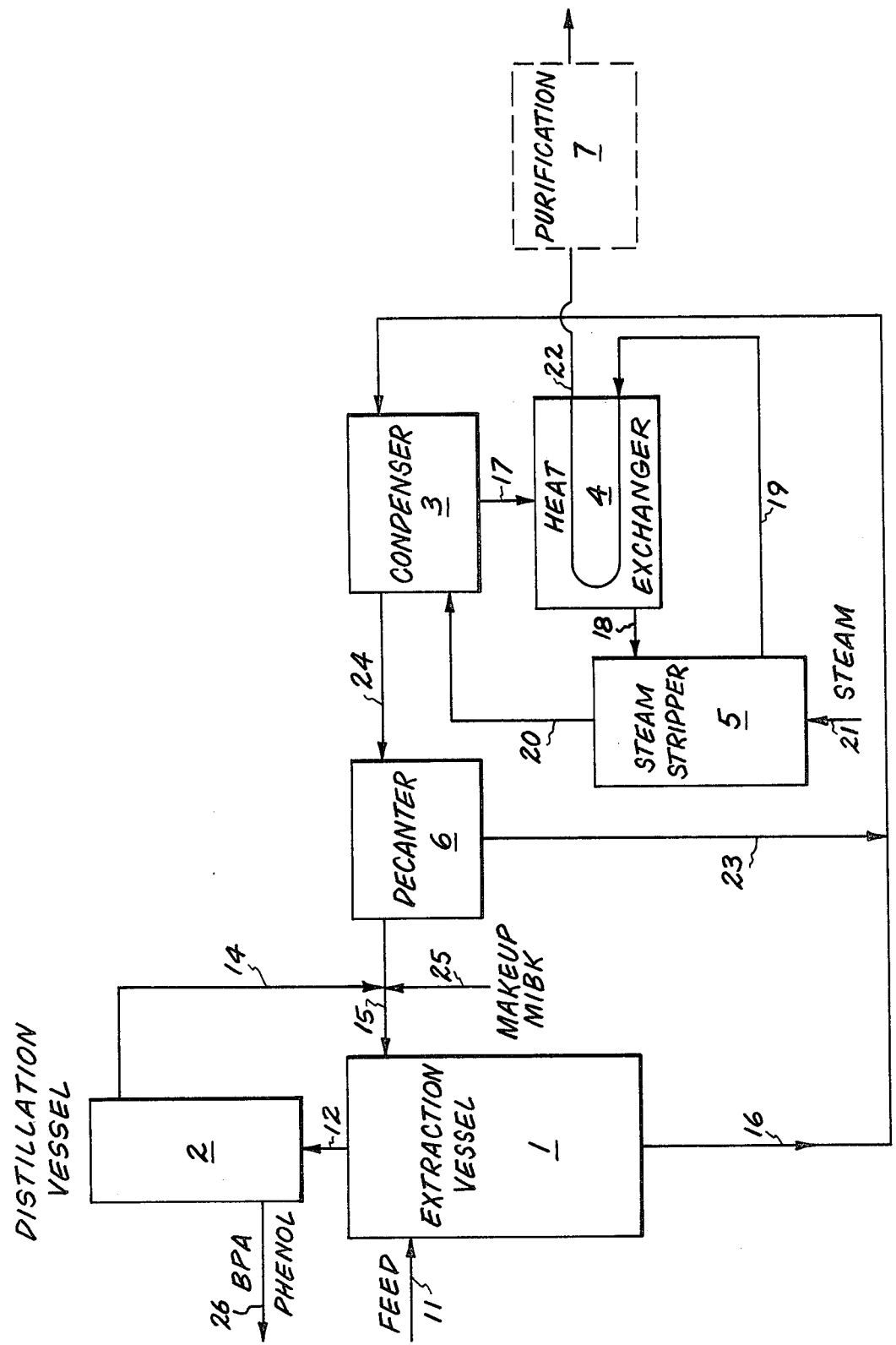

PURIFICATION OF AQUEOUS EFFLUENT STREAMS CONTAINING BPA AND PHENOL

This invention is concerned with the extraction of 2,2-bis (4-hydroxyphenyl) propane (hereinafter identified as "bisphenol A" or "BPA") and phenol from aqueous effluent streams. More particularly the invention is directed to the simultaneous extraction of BPA and phenol from aqueous effluent streams by liquid-liquid extraction using methyl isopropyl ketone hereinafter also known as "MIBK" as the extraction solvent, resulting in a substantially pure aqueous stream which can be disposed of without adverse environmental consequences.

BPA and phenol can be present, for example, in aqueous effluent streams from manufacturing processes which use BPA or phenol or where these compounds are produced as by-products. One such process is the process for preparing BPA from phenol and acetone. This reaction results in BPA which is accompanied by many impurities such as 2-(4-hydroxyphenyl)-2-(2-hydroxyphenyl) propane as well as other impurities including phenol itself. The BPA from this process is purified by using large amounts of water which dissolves substantially all of the phenol but leaves substantially all of the BPA. The waste water from this purification process containing phenol and BPA is in the form of a solution or mixture which requires considerable processing and expenditure of energy before it can be disposed of.

Phenol is among the more obnoxious of the contaminants which are present in the aqueous effluent from the aqueous purification process. Phenol has a taste and odor which are detectable in water at concentrations of less than 4 ppm, but gives an objectionable taste to fish at 1 ppm, and it is toxic to some species of fish at concentrations as low as 0.01 ppm. In addition, when water containing phenol is chlorinated, chlorophenols are produced which give the water an objectionable taste and odor at concentrations as low as 0.001 ppm. In general, the phenol content of industrial effluents is required to be less than 1 ppm. In the absence of any U.S. government regulatory standards on BPA its content in industrial effluents is assumed to also be less than 1 ppm.

Among the processes which can be used to remove BPA and phenol from aqueous effluent streams, solvent extraction is generally preferable over steam stripping for the removal of phenols, since the phenol-water system forms a minimum boiling azeotrope at 9.2 percent phenol, by weight. Activated carbon and resin bed adsorption have been used but the processing costs have become substantial at higher concentrations such as are encountered here. Reverse osmosis with cellulose acetate or thin-film composite membranes is not possible. Other permeators have a limiting phenol concentration of about 5,000 ppm above which they are impractical because of their inherent design features.

The solvent most suited for the extraction of phenol from water is methyl isobutylketone, hereinafter also referred to as MIBK, because of its high equilibrium distribution coefficient.

Measurements of the equilibrium distribution coefficients of BPA in phenolic water and MIBK, and phenol in BPA-water and MIBK, show that direct simultaneous extraction of BPA and phenol with MIBK is effective.

The equilibrium distribution coefficient ($K_d$) were measured for BPA between phenol plus water and MIBK, and for phenol between BPA plus water and MIBK. Batch extractions of BPA plus phenol from water by MIBK were performed in a constant temperature bath. Experiments were performed for varying temperatures less than 60° C., BPA concentrations less than 10% by weight BPA in the aqueous phase, and phenol concentration less than 6%, by weight phenol in the aqueous phase.

The equilibrium distribution coefficient at 30° C.±1° C. was found to be $\geq 2000$ for BPA between phenol plus water and MIBK, and $\geq 60$ for phenol between BPA plus water and MIBK. At 60° C.±1° C. the equilibrium distribution coefficient was $\geq 1000$ for BPA between phenol plus water and MIBK and $\geq 40$ for phenol between BPA plus water and MIBK.

In all cases a second extraction of the aqueous phase by MIBK was also performed. Since the BPA concentration in the aqueous phase was below the detection limit of the analyzer, the equilibrium distribution coefficient for BPA in phenol plus water was undetermined but the equilibrium distribution coefficient for phenol in BPA plus water was similar to the first extraction.

The equilibrium distribution coefficient of the solvent is very important since it affects the required ratio of solvent mass flow rate to aqueous mass flow rate in continuous extraction. The high distribution coefficient of MIBK allows efficient BPA and phenol extraction at relatively low solvent ratios and also allows efficient extraction with recycled MIBK which has been less thoroughly regenerated. Moreover the specific gravity of MIBK, 0.8 at 20° C., is sufficiently different from that of water, 0.989 at 20° C., so that countercurrent flow in a continuous extraction column or settling in a mixer-settler will proceed readily.

The extraction can be carried out in a conventional extraction column using countercurrent or cocurrent exchange flows. Countercurrent extraction is the preferred method. Using this method the heavy phase (water containing BPA and phenol) enters at the top, and the light phase (solvent MIBK) enters at the bottom of the column. The extract (MIBK containing BPA and phenol) is sent to distillation means to separate BPA and phenol from the MIBK. The column distillate is regenerated MIBK which is recycled to the extraction column. The BPA and phenol contained as a bottoms product from the distillation can be disposed of in any convenient manner or returned or recycled, for example, to the BPA process.

The water leaving the extraction column, as the raffinate phase, is saturated with MIBK and contains only trace quantities of BPA and phenol. This aqueous stream can be passed to a steam stripper to recover the MIBK. This MIBK would be recycled back to the extraction column for reuse. The effluent water containing trace quantities of BPA phenol and MIBK can be further purified, if needed, by activated charcoal or an organic resin.

It has been discovered that bisphenol A and phenol can be extracted simultaneously from aqueous effluent streams using methyl isobutyl ketone as the extracting solvent. By using MIBK in a liquid-liquid extraction an aqueous effluent stream containing BPA and phenol can be cleaned to a point where it can be disposed of in an environmentally safe manner without additional treatment. All of the chemicals, BPA, phenol, and MIBK, and water can be recovered in a substantially pure state for potential recycling. The BPA, phenol and MIBK can be separated and purified by subsequent distillation and vacuum steam stripping. There are both strong economic and strong environmental incentives for using this new process since large amounts of BPA and phenol can be conserved for possible recycling and in addition the resulting aqueous effluent stream can be cleaned of both BPA and phenol to a point where it can be disposed of in a conventional manner with little or no subsequent treatment and at minimum cost.

It has been discovered that the purification or cleaning of an aqueous effluent stream containing dissolved or suspend BPA and phenol can be accomplished by a continuous process for the simultaneous extraction of BPA and phenol using a liquid-liquid extraction with MIBK as the extraction medium. This purification is achieved by means of a continuous process comprising the following steps:

(a) introducing an aqueous stream containing BPA and phenol to an extraction vessel along with clean MIBK, (b) removing from the top of said extraction vessel an MIBK solution of BPA and phenol, (c) separating the BPA and phenol from said MIBK solution of BPA and phenol and recycling the MIBK to said extraction vessel, (d) removing the heavy aqueous phase from said extraction vessel and passing said aqueous phase to MIBK removal means where MIBK is separated and returned to said extraction vessel, and, (e) recovering from said MIBK removal means an aqueous phase which is substantially free of BPA, phenol and MIBK.

According to the present process there may be conveniently used aqueous solutions or suspensions containing dissolved or particulate BPA and phenol. Typical concentrations can range up to 30 percent BPA, by weight, and up to 15 percent phenol, by weight, and more particularly up to 10 percent BPA and up to 5 percent phenol, by weight.

Solutions with low concentrations of BPA and phenol such as those obtained from the aqueous purification steps of conventional BPA manufacturing processes are particularly suitable for use in the practice of this invention. The purified or cleaned aqueous phase obtained using the process of the present invention still contains trace quantities of MIBK, phenol and BPA which may optionally be removed by means of further processing steps, e.g. by passing the aqueous phase over activated charcoal or by using an organic resin.

The BPA and phenol recovered by distillation from the MIBK solution from the extraction vessel can be further separated from each other by distillation in separation distillation means. Using distillation to remove the BPA and phenol from the loaded solvent and to regenerate the solvent for reuse in the extraction vessel is attractive since the normal boiling point of MIBK, 119° C., is substantially lower than the very high boiling point of BPA which is 220° C., even at 4 mm Hg and phenol 181° C. In addition the high boiling impurities are prevented from accumulating in the recycle MIBK stream. Such an accumulation of impurities would change the distribution coefficients and the physical properties of the MIBK extraction solvent.

The temperature at which the liquid-liquid extraction vessel is operated will be based upon economic considerations and will generally fall within the range of 20° C. to 80° C. and more particularly between 25° C. and 35° C. For example, the temperature after the purification step in the manufacture of BPA is approximately 60° C. However, the solvent extraction process is more efficient at lower temperatures, e.g. approximately 30° C. In this case the cost of cooling the aqueous effluent of the purification step versus the lowered extraction efficiency at the higher temperature will dictate the extraction temperature used in individual processes.

By the use of the process of the present invention using liquid-liquid extraction with MIBK solvent for simultaneously extracting BPA and phenol from aqueous effluent streams it is possible to obtain substantially pure water by using only one solvent to extract both BPA and phenol resulting in great savings in the solvent, solvent recovery, and distillation costs when compared to a multiple solvent extraction process. The purified water can either be recycled or discharged directly since it can substantially conform with environmental effluent standards.

The weight ratio of MIBK extractant to aqueous feed streams will depend upon the concentration of BPA and/or phenol in the feed and the degree of purification desired. Typical ratios can range from 0.1 parts to 2.0 parts by weight MIBK per part of aqueous feed with a preferred ratio of about 0.5 parts, MIBK by weight per part of aqueous feed.

The present invention can be carried out in an apparatus as shown in the accompanying figure. An aqueous solution of BPA and phenol is fed via line 11 to a liquid-liquid extraction vessel 1 for extraction with MIBK which is supplied to the extraction vessel via line 15. The lighter MIBK phase from the extraction vessel which contains the extracted BPA and phenol is passed via line 12 to a distillation vessel 2 where MIBK is distilled from the BPA and phenol. BPA and phenol are removed via line 26 for optional separation and/or recycling or reuse and distilled MIBK is returned via line 14 for reuse for extraction in said extraction vessel. The heavier aqueous phase from said extraction vessel from which BPA and phenol have been extracted passes via line 16 to a condensor 3 where said aqueous phase is heated and then via line 17 to a heat exchanger 4 where additional heating takes place. The heated aqueous phase from said heat exchanger then passes via line 18 to a stream at a temperature of between 100° C. and 200° C. via line 21. Water vapor and MIBK vapor stripped from the aqueous phase are transferred via line 20 to said condenser 3 where the vapors are condensed after which the condensate is passed via line 24 to a decanter 6 in which the MIBK and water phases are allowed to separate after which the MIBK is recycled to said extraction vessel 1 via line 15. and the aqueous portion is passed via line 23 back to the stripping vessel 5 for additional steam stripping. Said aqueous product which is substantially free of BPA and phenol. The cleaned aqueous product may optionally be passed via line 22 through an additional purification stage 7 e.g. an activated carbon adsorber or organic resin bed which can remove additional BPA and phenol along with other contaminants.

In order that those skilled in the art may readily understand how the present invention may be practices, the following example is given by way of illustration and not by way of limitation.

EXAMPLE

The process of the present invention may be better understood by reference to the following description of a specific embodiment as applied to the accompanying drawings. An aqueous solution of 5% BPA and 5% phenol, by weight, is fed via line 11 to a countercurrent extraction column 1 which is maintained about 30° C., for liquid-liquid extraction using MIBK. Equal parts by weight of MIBK and aqueous feed are used. The light phase MIBK is passed via line 12 to a distillation column 2 operating at about 120° C. and at ambient pressure. BPA and phenol are removed as a bottom product via line 26 while MIBK is passed via line 14 for recycling to the extraction column 1. The heavy aqueous phase from the extraction column is passed via line 16 for heating through condensor 3 and heat exchanger 4 before being passed via line 18 to a steam stripping vessel 5 operating at one atmosphere pressure and supplied with fresh superheated steam at about 200° C. via line 21. The steam and MIBK vapor from said steam stripping vessel 5 is passed via line 20 through condensor 3 then via line 24 to decanter 6 where any water present in the condensate is separated. MIBK from said decanter 6 is passed via line 15 for reuse in the extraction column and the aqueous phase from said decanter 6 is passed via line 23 to line 16 for steam stripping. The aqueous phase form the steam stripping vessel 5 after substantially all the MIBK has been removed is passed via line 19 through heat exchanger 4 and an aqueous product which is generally free of MIBK and phenol is removed from the heat exchanger via line 22.

The purified aqueous phase can subsequently be passed to an optional purification step, if necessary, which uses activated charcoal or an organic exchange resin.

Other modifications and variations of the present invention are possible in light of the above teachings. It is, therefore, to be understood that changes may be made in particular embodiments described which are in the full intended scope of the invention as described in the appended claims.

What is claimed is:

1. A continuous process for purifying aqueous streams containing BPA and phenol comprising: introducing said aqueous effluent stream to an extraction vessel along with clean MIBK, removing from the top of said extraction vessel an MIBK solution of BPA and phenol, separating the BPA and phenol from the MIBK solution of BPA and phenol and recycling the MIBK to said extraction vessel, removing the heavy aqueous phase from said extraction vessel and passing said aqueous phase to MIBK removal means where MIBK is separated and returned to said extraction vessel, and recovering from said MIBK removal means an aqueous phase which is substantially free of BPA, phenol, and MIBK.

2. The process of claim 1 wherein the aqueous feed stream contains up to 30% BPA by weight and up to 15% phenol by weight.

3. The process of claim 1 wherein the aqueous feed stream contains up to 10% BPA by weight and up to 5% phenol by weight.

4. The process of claim 1 wherein the extraction vessel is operated at between about 20° C. and 80° C.

5. The process of claim 1 wherein the extraction vessel is operated at a temperature of between 25° C. and 35° C.

6. The process of claim 1 wherein the extraction vessel is operated at about 30° C.

7. The process of claim 1 wherein the energy consumed in the steam stripping process is recovered by means of heat exchangers.

8. The process of claim 1 wherein the MIBK is regenerated from the MIBK solution of BPA and phenol in a distillation vessel which is operated at about 120° C. and at about 1 atmosphere pressure.

* * * * *